United States Patent [19]

Kamen et al.

[11] Patent Number: 5,234,711
[45] Date of Patent: Aug. 10, 1993

[54] METHOD OF ENCAPSULATING PIGMENT PARTICLES USEFUL IN THE MANUFACTURING OF COSMETIC PRODUCTS AND THE PRODUCTS THEREOF

[75] Inventors: Melvin E. Kamen, Highlands; Philip Bernstein, Glen Ridge; Rene T. Rivero, West New York, all of N.J.

[73] Assignee: Revlon Consumer Products Corporation, New York, N.Y.

[21] Appl. No.: 845,784

[22] Filed: Mar. 6, 1992

Related U.S. Application Data

[63] Continuation of Ser. No. 498,514, Mar. 26, 1990, abandoned, which is a continuation-in-part of Ser. No. 418,361, Oct. 6, 1989, abandoned.

[51] Int. Cl.$^5$ .................... A61K 1/021; C09D 11/00; B01J 13/02
[52] U.S. Cl. .................... 427/213.34; 106/20 C; 523/105; 523/205; 424/401; 424/63; 424/64
[58] Field of Search ............... 523/160, 161, 205, 211, 523/105; 106/20; 427/213.34; 428/402.22, 402.24; 424/401, 497, 63, 64

[56] References Cited

U.S. PATENT DOCUMENTS

| | | | |
|---|---|---|---|
| 3,341,466 | 3/1967 | Brynko | 427/213.35 |
| 3,415,758 | 12/1968 | Powell | 427/213.33 |
| 3,441,353 | 4/1969 | Claff | 428/905 X |
| 3,516,943 | 6/1970 | Brynko | 264/4.3 |
| 3,619,842 | 11/1971 | Maierson | 264/4.3 X |
| 3,704,264 | 11/1972 | Gorman | 264/4.7 X |
| 3,714,012 | 1/1973 | Reiss | 204/404 |
| 4,069,604 | 9/1977 | Morehouse | 37/141 T |
| 4,421,660 | 12/1983 | Hajna | 252/62.54 |
| 4,447,475 | 5/1984 | Lubbock | 427/213.31 |
| 4,450,304 | 5/1984 | Diery et al. | 252/351 X |
| 4,608,401 | 3/1986 | Martin | 503/205 |
| 4,665,107 | 5/1987 | Micale | 523/105 |
| 4,680,200 | 7/1987 | Solc | 427/213.34 |
| 4,783,333 | 2/1988 | Mercado | 424/63 |
| 4,798,691 | 1/1989 | Kasai | 428/402.22 X |
| 5,013,543 | 5/1991 | Mercado et al. | 424/63 |

FOREIGN PATENT DOCUMENTS

| | | | |
|---|---|---|---|
| 2107429 | 9/1971 | Fed. Rep. of Germany | 424/63 |
| 1027913 | 2/1986 | Japan | 424/63 |

Primary Examiner—Robert L. Stoll
Assistant Examiner—John M. Covert
Attorney, Agent, or Firm—Julie Blackburn

[57] ABSTRACT

A method for the encapsulation of pigment particles utilized in ink formulations by means of vinyl polymerization, within an aqueous medium, and the cosmetic products prepared with said ink formulations are disclosed. The method of encapsulation can be either that of free-radical polymerization, wherein a peroxide catalyst and a antioxidant are employed or that of a redox system wherein an ion-producing metallic pigment is utilized. The resultant cosmetic products are characterized by their overall smoothness, uniform color, and increased dispersibility of the ink formulations utilized therein, and, due to the presence of the ink formulation having the encapsulated pigment particles dispersed therein.

13 Claims, No Drawings

METHOD OF ENCAPSULATING PIGMENT PARTICLES USEFUL IN THE MANUFACTURING OF COSMETIC PRODUCTS AND THE PRODUCTS THEREOF

CROSS REFERENCE TO RELATED APPLICATIONS

This is a continuation of copending application(s) Ser. No. 07/498,514 filed on Mar. 26, 1990 now abandoned, which is a continuation-in-part of copending application Ser. No. 07/418,361, filed Oct. 6, 1989 now abandoned.

FIELD OF THE INVENTION

This invention relates to inks having therein pigment particles encapsulated with a polymer; and to the method of producing the same; said inks being useful in the manufacturing of cosmetic products.

BACKGROUND OF THE INVENTION

The use of inks is well known throughout a variety of industries. For instance, in the cosmetic industry various products such as eyeliner, eyeshadow pencils, lipstick, emollients, toners, and certain other types of cosmetic compositions call for the use of some form of colorant such as an ink or at least one pigment and/or a dye. The insoluble pigments, including the noncertifiable inorganic types as well as those classified within the broader category of certified organic pigments are the most widely used colorants. Depending upon the desired finished cosmetic product, the inks or combinations thereof are incorporated within the particular formulations by grinding, dispersing, mixing, and, at times, extended by use of mechanical apparatus such as hammer mills, roller mills, ball mills, colloid mills, mortars, micropulverizers, and any other suitable conventional means. Regardless of the ink or suitable derivative thereof selected and the means of incorporation utilized therefor, the suitability of the particular colorant is determined by the intended use of the final product.

In order to be useful in the preparation of cosmetic products, the selected ink(s) must exhibit particularly desired physical and chemical characteristics. Among these characteristics of greatest concern are included light and pH stability, good resistance to oxidizing and reducing, as well as to alkali and weak acids, and dispersibility, particularly, grindibility. The latter three interrelated characteristics are of most particular interest, because they impart the desired results of dispersibility, uniformity and smoothness in the finished product, when applied to the skin of the consumer.

Some pigment particles within the ink, due to their inability to be "wetted down" by the ointment, are incapable of yielding a desired uniform, if not homogeneous, final composition. In such cases, the pigment base contains particles which tend to float to the top thereby resulting in a non-uniform composition which is unappealing to the consumer. This problem can sometimes be remedied by the incorporation of minute quantities of organic pigments. However, the addition of organic pigments tends to yield an undesirably more intense color, upon application. Oftentimes, as a result of their inherent indispersibility, the use of certain pigment bases such as, in particular, those utilized in eyeliner and eyeshadow pencil formulations, result in undesirable entrapment of air bubbles. This problem can usually be overcome by heating the mixture to approximately 70° Centigrade under slow stirring. Since the determination as to complete evacuation of air bubbles is virtually a matter of periodic "pulldown", i.e., smear testing, on a glass slide or a piece of paper, the foregoing combined heat and stir method of removing entrapped air bubbles presents the trial and error risk problem of possible inadvertent prolonged heating and excessive agitation. Also, it is obvious that any additional remedial steps can ultimately become time consuming and therefore somewhat costly.

A yet further problem often encountered in the use of certain pigment-base inks is that of undesirable color change of the particles, due to inherent structural alteration during milling. For instance, ferrous oxide tends to lighten to a dark-brownish shade. This phenomenon occurs as a result of the temperature increase during milling. Hence, there is a widespread need, particularly, in the cosmetic industry, for a method wherein smaller pigment particles can be obtained to circumvent the problems of the prior art. Accordingly, it is desirable to provide a pigment-base ink which is void of the abovementioned drawbacks, yet foreseeably useful in virtually all industrial applications wherein conventional inks are called for.

It is an object of this invention to provide a method for the polymeric encapsulation of unusually smaller, uniform pigment-base particles.

It is a further object of this invention to provide an improved pigment-based ink which exhibits the desired properties of increased wettability, i.e., dispersibility, and heat resistance, with concommittant color stability.

It is also a further object of this invention to provide an improved pigment-based ink which is particularly useful throughout, but not limited to, the cosmetic industry.

It is a still further object of this invention to provide improved cosmetic products, due to the incorporation therein of inks having polymer encapsulated pigment particles therein which were prepared, in accordance with this invention.

SUMMARY OF THE INVENTION

This invention relates to a method of encapsulating pigment particles useful in inks by means of redox, or free-radical vinyl polymerization, in an aqueous medium; the inks having therein the encapsulated pigment particles obtained thereby; and the usefulness of said inks in the manufacturing of cosmetic products.

DETAILED DESCRIPTION OF THE INVENTION

Since the methods of preparation of the encapsulated pigment particles disclosed herein, the ink compositions in which said encapsulated pigment particles are utilized; and the cosmetic products obtained therewith are adequately described, it is felt that drawings are not required in the present specification.

The pigment-based inks employed are widely utilized for coloration in eyeliner and eyeshadow formulations. Such pigments must comply with the Federal Food, Drug and Cosmetic Act and therefore must either be inorganic or a natural color. Also, they must be insoluble in water. For example, suitable pigment bases include iron oxide black (ferric oxide), and ferrous oxide, (sienna shade and ochre shade), ultramarine blue or Prussion blue, chromium oxides, chromium hydroxide, carmine F. F. (aluminum lake of the cochineal pigment), zinc oxide, silica, and manganese violet. Additional examples include talc, mica, titanium dioxide; and any of the foregoing carried on the surface of talc, mica, or titanium oxide; and titanated mica. The term "pigment" may include mixtures of two or more of the foregoing.

In the preparation of the encapsulated pigment particles for use in ink formulations, in accordance with this invention, the source of the pigment can be that found in various commercially available forms. For instance, a selected pigment may be obtained in its isolated form or, in that of a composition such as a "pressed cake"

As discussed in Cosmetics, Science and Technology by Balsam and Sagarin et al., Vol. 3 (1974) the selected pigment dispersion may depend on the particular type of cosmetic product in which it is to be employed. For example, in the manufacturing of face powder, the color may be "fully extended" by hammer milling or micropulverizing the pigment with talc and other colorless ingredients. In the preparations of other makeups and lipstick, the color additive may be admixed with a homogenizer and, optionally, ground on a colloid mill. In the case of nail lacquer, a nitrocellulose base may be combined with the pigment, and the resultant mixture ground on a ball mill.

A typical preparation of a commercially available ink useful as a marking material for eyeliner would entail the following steps: admixing required amounts of colorants such as ultramarine, chromium oxide green and iron oxide (sienna green), with titanium oxide or zinc oxide with a melted fatty material such as petrolatum; then grinding the mixture in a roller mill; heating the oil, melting additional fatty materials such as lanolin, and a basic ingredient such as ceresin in a separate container; and thereafter adding the color paste to the oil, fatty material, and basic ingredient mixture.

As previously mentioned, the present invention can optionally employ a redox or free-radical vinyl polymerization, in an aqueous medium, to encapsulate pigment particles for use in ink formulations. As a result of the polymerization the "wettability", i.e., dispersibility of the thusly encapsulated particles is substantially improved. Upon incorporation in an ink formulation and the subsequent utilization thereof in a cosmetic product, the encapsulated pigments disclosed herein yield desirable finishes characterized by their improved dispersibility, overall smoothness, and uniform colorization.

Since the mechanism by which the vinyl polymerization can optionally be carried out, according to this invention, involves a redox system, it is necessary that, in addition to the mono-substituted vinyl monomer, an oxidizing agent and a reducing agent be present. Since an emulsion could form because of monomer water immiscibility, an organic surfactant is required to stabilize the emulsion. The usefulness of certain metallic reductants capable of undergoing single-electron transfer stage-type redox reactions is discussed below.

Among the useful vinyl monomers are included those compounds having the characteristic mono-substituted ethylene group such as N-vinylpyrrolidone, propylene, n-butylacrylate, vinyl acetate, styrene, methylmethacrylate as well as other acryloid compounds.

For the purposes of this invention a catalytic peroxide is utilized as the oxidizing agent or oxidants and a hydroxyalkane inorganic acid salt such as sodium formaldehyde sulfoxalate, as the reducing agent.

Among the useful oxidants are included benzoyl peroxide, t-butylhydroxyperoxide, hydrogen peroxide, and perbenzoic acid.

Among the useful reducing agents are included sodium formaldehyde sulfoxalate and those metallic compounds in the proper oxidation state which yield the radical destroying ions such as iron, manganese, and copper.

The aforementioned surfactants which are useful in the practice of this invention are those nonionic compounds having high "HLB" numbers. The terminology "HLB Nos." refers to the hydrophilic-lypophilic balance. The numerical assignment of the HLB of a particular surface acting compound is based on a scale between 1 and 20, wherein the low end of the scale indicates oil solubility and the high end, water solubility. A more detailed discussion of the hydrophilic-lipophilic balance (HLB) is disclosed in the Encyclopedia of Polymer Science and Engineering, Volume 6 (Emulsion Polymerization, p.25).

Among the surfactants useful in the practice of this invention are included the emulsifier and/or stabilizer type alkyleneoxy alcohols and alkylphenol alkoxylates having HLB Nos. from 12 to 20. Among the preferred surfactants, in accordance with this invention, are included commercially available compounds having HLB numbers from 17 to 19 such as Igepal CO-997 (a nonylphenoxypoly(ethyleneoxy)ethanol produced by the GAF Chemicals Corp.) and octyl phenoxyethoxylate.

In the preparation of the encapsulated pigments to be utilized in ink formulations, according to this invention, one would admix, in a suitable reaction vessel such as a three-neck Morton Flask equipped with a stirrer and a reflux condenser, thermometer and dropping funnels about 40% percent, by weight, of water, about 7 to about 9 percent of the mono-substituted, ethylenically unsaturated monomer, and about 42 to about 44 percent of the pigment component under ambient conditions for a period of about 0.5 hour to obtain homogeneity. Then about 0.75 to about 1.2 percent, by weight of the oxidizing agent, and about 0.50 to 0.75 percent of the reducing agent (charge) are added to the reaction mixture as the temperature thereof is increased to and maintained at between 65° and 70° C. for approximately 3.0 hours. Thereafter two additional charges of the aforesaid catalytic antioxidant and reducing agent are added to the reaction mixture, as moderate stirring at about 200 rpm is continued over a period of approximately 6.0 hours at a temperature of about 60° C.

While the presence of encapsulation and the extent thereof can be determined by sophisticated means such as electronmicroscopy or some other technique of investigative macromolecular structures, a Hegman Gauge is readily useful therefor. This instrument which is widely utilized throughout the cosmetic product industry and many others such as those of ink and paint consist of a rectangular metal plate which is slightly grooved and has a graduated scale imprinted thereon. The grove is designed so that it gradually inclines at a rate commensurate to that of the aforesaid scale. The sample material is "pulled down", i.e., smeared, in one direction parallel to the scale which is downwardly graduated to indicate descending particle size. (See ASTM Standards, Sec. 6, Vol. 06.01, (1983) pp. 194–195).

Among the useful inorganic pigments are included iron oxide, titanium dioxide, chromium dioxide, chromium hydroxide, zinc oxide, hexakis (cyano-C) ferrate (4-) (Prussian blue), talc, mica, silica kaolin, manganese violet, ultramarine violet, and suitable substitutes or combinations thereof.

Among the useful anhydrous alcohols for the preparation of the inks in the practice of this invention are included methanol, propanol, and isopropanol.

As an alternate embodiment of the present invention, the encapsulation process can be carried out, without the use of a reductant such as sodium formaldehyde sulfoxalate, using a pressed cake which contains a combination of ferric oxide and ferrous oxide as the pigment component. The ferrous ions present in the pressed cake act as the reducing agent in the redox vinyl-polymerization system. Small amounts of the mono-substituted ethylenically unsaturated monomer and the peroxide catalyst are simultaneously stirred into the reaction mixture.

In the practice of this invention, it is preferred that the pigment base be a combination of ferric oxide and ferrous oxide such as that found in a commercially available pressed cake. It is also preferred that said pressed cake be utilized in an amount having from 10 to about 75 percent, by weight, of the iron oxide pigment. As a result of the combined thermoreactivity of the polymerization and the heat caused by the shearing, the size of the pigment (iron oxide) particles is reduced to between 1 to 15 microns. This method therefor obviates the need for subsequent grinding, e.g. ball milling.

With respect to the useful mono-substituted ethylenically unsaturated monomer, i.e., vinyl-monomer, it is preferred that N-vinylpyrrolidone, styrene or combinations thereof be utilized in amounts such that the weight ratio of pigment to polymer [ratio] is from 20:1 to 1:1, respectively.

Regarding the catalytic antioxidant, i.e., oxidizing agent, it is preferred that tertbutylhydroxyperoxide or benzoyl-hydroxyperoxide be utilized in an amount of from 0.75 to about 1.2 percent of the total weight of the reaction mixture.

In the absence of reductant metallic ions such as from ferrous oxide as referred to, supra, in the redox polymerizations of this invention, it is preferred that a hydroxyalkane salt of an inorganic acid such as sodium formaldehydehydroxysulfoxylate be employed as a reducing agent. Said reducing agent is to be present in an amount of about 0.50 to about 0.75 percent, by weight, of the total reaction mixture.

A particular advantage of the present invention is that the vinyl-polymeric encapsulation process provides a means for increasing the wettability of the pigment particles. Hence, the characteristics of improved dispersibility affords a means by which the resultant encapsulated pigment particles are more readily useful in a broad range of commercial preparations. In particular, the encapsulated pigment particles are useful in a wide variety of cosmetic products such as eye liner, eye shadow, lipstick, complexion powders, creams and lotions as well as virtually all forms of facial makeup and hair applications.

Cosmetic products derived from such encapsulated pigments display desired characteristics such as generally improved colorization, e.g., uniformity, shade intensity and truer colors. In addition to the foregoing, the final cosmetic products having one or more of the encapsulated pigments embodied herein are smudge-proof, upon drying, yet, easily removable by water.

It will be understood that the embodiments described herein are merely exemplary and that a person skilled in the art may make variations and modifications without departing from the spirit and scope of the invention.

The following examples further illustrate certain aspects of the present invention and are not intended to limit the scope thereof to such.

EXAMPLES I-III

A sufficient quantity of encapsulated pigment was prepared, in accordance with this invention, for use in black eyeliner pens. In this instance, two ethlylenically unsaturated monomers were reacted, in the presence of an alkyl hydroxyperoxide and alkylphenoxypoly(ethyleneoxy) alcohol to encapsulate the pigment particles as follows:

A water bath was pre-heated to 176° F. A two liter, three-neck Morton Flask which is a vessel having baffled sides, was prepared for use as follows:

The opening of the central neck of the flask was equipped with a mechanized stirrer. Each of the two lateral necks respectively located on opposite sides of the central opening was provided with a Claisen Adaptor. A thermometer was fitted into the primary opening of one of the adapters and downwardly extended so that the thermosensitive bulb end thereof would be submerged within the reaction mixture. A first drop-ping funnel was inserted into the secondary opening which extends laterally from the flow channel of the primary opening.

A second dropping funnel was inserted into the primary opening of the second adapter, and the laterally extended opening thereof was fitted with a reflux condenser.

Approximately, 270 g of water, 546 g of a pressed cake black, 108 g of nonylphenoxypoly(ethlyeneoxy)ethanol and 35 g N-vinylpyrrolidone were introduced into the flask and moderately stirred to form a homogeneous mixture. The flask containing the foregoing mixture was then placed into the water bath. The thusly prepared mixture was charged by slowly admixing therein a solution consisting of 2.6 grams of tert-butylhdroxyperoxide in 20 milliliters of water and a comonomeric mixture consisting of an additional 24 grams of N-vinylpyrrolidone and 251 grams of vinyl acetate.

The above-described comonomeric mixture was fed into the reaction mixtures by means of a dropping funnel at a rate of 4 ml per minute. The resultant polymerizable mixture was continuously stirred as the pH thereof was adjusted from 5.8 to 7.0 by the dropwise addition of ammonium hydroxide, while the temperature therein was maintained at about 175° F. over a period of about 2½ hours. During the final half hour the temperature was increased to 185° F. to assure complete polymeric encapsualtion of the pigment particles. Completion of the reaction was indicated by the absence of any reflux. Thereafter the temperature of the reaction mixture was decreased to about 175° F., and the reaction vessel was removed form the water bath. Then the pH of the reacted mixture was readjusted to 7/0 from 5.2 by the addition of ammonium hydroxide solution.

Quantities of the encapsulated pigment particles prepared in the manner described hereinabove were subsequently utilized to prepare a series of eyeliner inks. In each instance, the respective eyeliner ink formulations were prepared in separate containers using conventional additives as set forth in the following chart.

| Additives | Ink Formulation (amounts in grams) | | |
|---|---|---|---|
| | A | B | C |
| Encapsulated Pigment | 40.0 | 60.0 | 60.0 |
| Hydrous Alcohol | 10.0 | 15.0 | 5.0 |
| Propylene Glycol | 3.0 | 4.5 | 4.5 |
| Polyoxyethylene (20) Sorbitan monolaurate | 2.0 | 3.0 | 2.0 |
| Phenoxyethanol | 0.5 | 0.75 | 0.75 |
| Water | 44.5 | 15.75 | 15.75 |

When the above-described ink formulations were utilized in conventional eyeliner pens, they exhibited the desired characteristics of smoothness and uniform color. In particular, the eyeliner ink pens prepared with formulations A and C wetted-out rapidly and displayed dark payoffs as a result of the presence of the more dispersible encapsulated pigment particles.

EXAMPLE IV

An additional quantity of encapsulated pigment was prepared, in accordance with this invention. In this instance, a water soluble vinyl compound was utilized as the mono-substituted monomer, in combination with an alkylhydroxyperoxide, to encapsulate the pigment particles. A surfactant such as an emulsifier was omitted, due to the presence of the aforesaid water soluble polymerizable vinyl monomer. The instant preparation which was performed in a matter similar to that described in Examples I–III hereinabove was as follows:

A waterbath was heated to 175° Fahrenheit. In place of the 1.5 liter flask utilized in Example I–III, a 500 milliliter resin flask, i.e., Morton Flask, was employed. In this instance, the initial reaction mixture comprised 170 grams of water, 150 grams of Mapico Red 297 (a commercially available ferric oxide) in the form of a commercially available press cake produced by the Columbia Corporation of St. Louis, Mo., and 30 grams of N-vinylpyrrolidone. The mixture was stirred at 200 rpm for approximately one half hour at ambient temperature. Thereafter 4 milliliters of a solution comprising 1.3 milliliters of t-butylhydroxyperoxide in 10 milliliters of water was added. Then 3 milliliters of sodium formaldehydesulfoxylate was added to the reaction mixture as the temperature therein was adjusted to 65° Centigrade. The reaction mixture was maintained at a temperature ranging between 65° and 70° Centigrade over a period of about 3 hours. Thereafter an additional 4 milliliters of the t-butylhydroxyperoxide solution and 3 milliliters of the sodium formaldehydesulfoxylate solution were added. The reaction vessel was then maintained at a temperature of about 60° Centigrade for a period of about 1 hour, while stirring was continued at 200–300 rpm. Following an additional 4 hour reaction period additional "charges" of the aforesaid respective oxidizing and reducing agent were added as stirring was continued for an additional hour. Throughout the polymerization reaction the resin flask remained uncovered. This resulted in the evaporation of approximately half of the original 170 grams of water which was utilized at the start of the procedure.

The thusly prepared aqueous suspension of encapsulated pigment particles was thereafter analyzed. Upon observation, it was observed that the reaction mixture had become a creamy suspension of very fine particles of the pigment comparable to those obtained in Examples I–III hereinabove which were subsequently utilized in the preparation of eyeliner ink pens.

EXAMPLE V

The procedural steps set forth in Example IV hereinabove were repeated, except in place of the Mapico Red a commercially available yellow press cake was utilized as the pigment component. Also, the respective amounts of the ingredients and reaction conditions differed as follows: The composition of the reaction matter consisted of 500 grams of water, 70 grams of N-vinylpyrrolidone, 6 milliliters (hereinafter ml) of t-butylhydroxyperoxide and 4 ml of sodium formaldehydesulfoxylate. The foregoing mixture was stirred at a rate of 470 rpm for about 20 minutes as the temperature therein was gradually increased from about 40° Centigrade to about 58.4° Centigrade. The pH thereof was increased from 6.2 to 7.2 by the addition of 40 drops of ammonium hydroxide, and the reaction vessel was removed from the heating mantle. The stirring was continued at 440 rpm as 1 drop of t-butylhydroperoxide, 3 ml of sodium formaldehydesulfoxylate, and 1 ml of t-butylhydroxyperoxide were added. Thereafter the reaction mixture was allowed to cool to room temperature. Upon subsequent testing in the manner described in Example IV hereinabove, it was observed that the drawdown of the resultant mixture was uniformly smooth and silky, and there was no evidence of coarse particles. The Hegman Gauge reading of this formulation approached 8, indicating an outstanding particle size of from 1 to 5 microns.

EXAMPLE VI

This example illustrates the polymeric encapsulation, in accordance with this invention, wherein a phosphatide-type surfactant is utilized in a free-radical polymerization as set forth hereinbelow.

The procedural steps set forth in Example IV hereinabove were repeated, except in place of the Mapico Red 400 grams of a commercially available red iron oxide was utilized as the pigment component. Also, the respective amounts of the ingredients and reaction conditions differed as follows:

In addition to the aforesaid quantity of pigment component, the composition of the reaction matter consisted of 350 grams of water, 80 grams of N-vinylpyrrolidone, 6 milliliters (hereinafter ml) of t-butylhydroxyperoxide and 5 ml of sodium formaldehydesulfoxylate, and 8 grams of lecithin. The foregoing mixture was stirred at a rate of 470 rpm for about 20 minutes as the temperature therein was gradually increased from about 64° Centigrade to about 58.4 Centigrade. The pH thereof was increased from 6.2 to 7.2 by the addition of 40 drops of ammonium hydroxide, and the reaction vessel was removed from the heating mantle. The stirring was continued at 440 rpm as 1 drop of HAC, 3 ml of sodium formaldehydesulfoxylate, and 1 ml of t-butylhydroxyperoxide were added. Thereafter the reaction mixture was allowed to cool to room temperature. Upon subsequent testing in the manner described in Example IV hereinabove, it was observed that the drawdown of the resultant mixture was uniformly smooth and silky, and there was no evidence of particles.

Summarizing, it is thus seen that this invention provides alternate, novel methods for polymeric encapsulating pigment particles for the preparation of inks which are readily useful in the manufacturing of cosmetic products. The encapsulated pigment particles, according to this invention, can be prepared either by free-radical polymerization of a mono-substituted monomer or by means of a redox reaction, using an ion-producing metallic pigment. Regardless of which method of polymeric encapsulation is utilized the inks prepared with the resultant encapsulated pigment particles, can be used in the manufacturing of improved cosmetic products. Such cosmetic products are characterized by their ability to maintain smoothness, water repellency, and yet be removable by water, when applied to the skin of the consumer.

It will be understood that the embodiments described herein are merely exemplary and that a person skilled in the art may make many variations and modifications without departing from the spirit and scope of the invention.

Based on the disclosure set forth hereinabove it will become apparent to those skilled in the art that various modifications in procedures, proportions, and materials may be made, without departing from the scope and spirit thereof, as defined by the following claims.

We claim:

1. A method of encapsulating finely divided clumped or agglomerated ion-producing metallic pigment particles by means of a redox polymerization, which eliminates the need for pulverizing or grinding said pigment particles, comprising the steps of:
   (a) agitating a mixture of N-vinyl pyrrolidone monomer, a surfactant having an HLB of 12-20, and an ion-producing metallic pigment in an aqueous medium wherein the pigment to polymer ratio is 20:1 to 1:1,
   (b) adding an amount of a peroxide catalyst to said mixture obtained in step (a) and,
   (c) thereafter heating the resultant mixture obtained in step (b) to a temperature of about 175° F. and adjusting the pH to about 7.0, and maintaining the same at a temperature of about 175° F. for at least two hours,
   (d) readjusting the pH of the mixture to 7.0 to form an aqueous slurry of discrete encapsulated pigment particles of 1 to 15 microns in diameter.

2. The method of claim 1 wherein said ion-producing metallic pigment is selected from the group consisting of ferric oxide, a combination of ferrous oxide and ferric oxide, and manganese violet.

3. The method in accordance with claim 1 wherein said ion-producing metallic pigment is ferric oxide.

4. The method of claim 1 wherein 40-60% of the encapsulated pigment slurry is mixed with 5-15% anhydrous alcohol in an aqueous base to form an ink.

5. An ink composition consisting essentially of 46-60% N-vinyl pyrrollidone polymer encapsulated ion-producing metallic pigment particles, 20-30% anhydrous alcohol, and 10-20% propylene glycol; wherein the pigment particles have been encapsulated by:
   (a) agitating a mixture of N-vinyl pyrrolidone monomer, a surfactant having an HLB of 12-20, and an ion-producing metallic pigment in an aqueous medium,
   (b) adding an amount of a peroxide catalyst to said mixture obtained in step (a) and, p1 (c) thereafter heating the resultant mixture obtained in step (b) to a temperature of about 175° F. and adjusting the pH from 5.8 to 7.0, and maintaining the same at a temperature of about 175° F. for at least 2 hours;
   (d) increasing the temperature to about 185° F. for about a half hour;
   (e) decreasing the temperature to about 175° F.
   (f) readjusting the pH of the mixture to 7.0 to form an aqueous slurry of encapsulated pigment particles of 1 to 15 microns in diameter.

6. The ink composition in accordance with claim 5 wherein said anhydrous alcohol is selected from the group consisting of methanol, propanol, and isopropanol.

7. The ink composition in accordance with claim 5 wherein said polymer encapsulated pigment particles is present in an amount, based on the total composition, of from 40 to 60 percent, and said anhydrous alcohol is present in an amount of from 20.0 to 30.0 percent and said propylene glycol is present in an amount of from 10.0 to 20.0 percent.

8. The ink composition in accordance with claim 5 further including polysorbate 20 (polyoxyethylene 20 sorbitan monolaurate) and phenoxyethanol.

9. The ink composition in accordance with claim 8 wherein said polysorbate 20 (polyoxyethylene 20 sorbitan monolaurate) is present in an amount, based on the total composition, of from 2.0 to 3.0 percent and said phenoxyethanol is present in amount of from 0.5 t 0.75 percent.

10. An ink composition consisting essentially of, based on the total weight of said composition, from 40 to 60 percent of N-vinyl pyrollidone polymer encapsulated pigment particles, form 5.0 to 10.0 percent of an anhydrous alcohol, from 3.0 to 4.5 percent of propylene glycol, from 2.0 to 3.0 percent of polysorbate 20 (polyoxyethylene 20 sorbitan monolaurate) and from 0.5 to 0.75 percent phenoxyethanol; wherein the pigment particles have been encapsulate by:
   (a) agitating a mixture of N-vinyl pyrrolidone monomer, a surfactant having an HLB of 12-20, and an ion-producing metallic pigment in an aqueous medium,
   (b) adding an amount of a peroxide catalyst to said mixture obtained in step (a) and,
   (c) thereafter heating the resultant mixture obtained in step (b) to a temperature of about 175° F. and adjusting the pH from 5.8 to 7.0, and maintaining the same at a temperature of about 175° F. for at least 2 hours;
   (d) increasing the temperature to about 185° F. for about a half hour;
   (e) decreasing the temperature to about 175° F.
   (f) readjusting the pH of the mixture to 7.0 to form an aqueous slurry of encapsulated pigment particles of 1 to 15 microns in diameter.

11. A method for preparing inks containing therein N-vinyl pyrollidone encapsulated ion producing metallic pigment particles of 1 to 15 microns in diameter which eliminates the need for pulverizing said pigments comprising the steps of:
   (a) agitating a mixture of N-vinyl pyrollidone monomer and an ion producing metallic pigment in an aqueous medium,
   (b) adding peroxide catalyst to said mixture obtained in step (a)
   (c) thereafter heating the resultant mixture obtained in step (b) to a temperature of about 175° F. and adjusting the pH of the mixture from 5.8 to 7.2, and maintaining the same at a temperature of about 175° F. for at least 2 hours;
   (d) increasing the temperature to about 185° F. for about a half hours;
   (e) decreasing the temperature to about 175° F.

(f) readjusting the pH of the mixture to 7.0 to form an aqueous slurry of encapsulated pigment particles, (g) admixing 40–60% of the slurry obtained in step (f) with 20–30% anhydrous alcohol in an aqueous base to thereby produce an ink.

12. The method of claim 11 wherein a surfactant of HLB 12–20 is mixed with the pigment and N-Vinylpyrollidone in step (a).

13. A cosmetic composition containing N-vinylpyrrolidone encapsulated ion-producing metallic pigment particles of 1 to 15 microns in diameter which are encapsulated by:

(a) agitating a mixture of N-vinylpyrrolidone monomer, a surfactant having an HLB of 12–20 and an ion-producing metallic pigment in an aqueous medium wherein the pigment to polymer ratio is 20:1 to 1:1, (b) adding an amount of a peroxide catalyst to said mixture obtained in step (a) and, (c) thereafter heating the resultant mixture obtained in step (b) to a temperature of about 175° F. and adjusting the pH of the mixture to about 7.0, and maintaining the same at a temperature of about 175° F. for at least 2 hours;

(d) readjusting the pH of the mixture to 7.0

(e) adding the pigment particles to a cosmetic composition.

* * * * *